US012790638B2

(12) United States Patent
Le Goff et al.

(10) Patent No.: US 12,790,638 B2
(45) Date of Patent: Nov. 10, 2026

(54) METHOD FOR THE DETECTION OF POLYCYCLIC AROMATIC HYDROCARBONS

(71) Applicants: CENTRE NATIONAL DE LA RECHERCHE SCIENTIFIQUE, Paris (FR); UNIVERSITE GRENOBLE ALPES, Saint Martin d'Heres (FR)

(72) Inventors: Alan Le Goff, Crets-en-Belledonne (FR); Ilaria Sorrentino, Nice (FR)

(73) Assignees: CENTRE NATIONAL DE LA RECHERCHE SCIENTIFIQUE, Paris (FR); UNIVERSITE GRENOBLE ALPES, Saint Martin d'Heres (FR)

( * ) Notice: Subject to any disclaimer, the term of this patent is extended or adjusted under 35 U.S.C. 154(b) by 666 days.

(21) Appl. No.: 18/264,097

(22) PCT Filed: Feb. 2, 2022

(86) PCT No.: PCT/EP2022/052472
§ 371 (c)(1),
(2) Date: Aug. 3, 2023

(87) PCT Pub. No.: WO2022/167479
PCT Pub. Date: Aug. 11, 2022

(65) Prior Publication Data
US 2024/0093264 A1 Mar. 21, 2024

(30) Foreign Application Priority Data
Feb. 4, 2021 (EP) .................................... 21305146

(51) Int. Cl.
*C12Q 1/26* (2006.01)
*C12Q 1/00* (2006.01)

(52) U.S. Cl.
CPC ............... *C12Q 1/26* (2013.01); *C12Q 1/005* (2013.01)

(58) Field of Classification Search
CPC ...... C12Q 1/26; C12Q 1/005; G01N 33/0013; G01N 33/1826
See application file for complete search history.

(56) References Cited

U.S. PATENT DOCUMENTS

2021/0050613 A1 2/2021 Holzinger et al.

FOREIGN PATENT DOCUMENTS

WO 2019175426 9/2019

OTHER PUBLICATIONS

Lalaoui et al. ("Wiring Laccase on Covalently Modified Graphene: Carbon Nanotube Assemblies for the Direct Bio-electrocatalytic Reduction of Oxygen", Chem. Eur. J. 2015, 21, 3198-3201). (Year: 2015).*

(Continued)

*Primary Examiner* — Ali Z Fadhel
(74) *Attorney, Agent, or Firm* — Chrisman Gallo Tochtrop LLC

(57) ABSTRACT

A method for the detection of polycyclic aromatic hydrocarbons including: a) a step of contacting an aqueous solution including at least one polycyclic aromatic hydrocarbon with a catalyst for the oxidation of polycyclic aromatic hydrocarbons and with an electrode made of a conductive porous material, and b) a step of detecting the anthraquinone that is formed during the previous step through the oxidation of the polycyclic aromatic hydrocarbons.

10 Claims, 3 Drawing Sheets

(56) References Cited

OTHER PUBLICATIONS

Kumar ("Biological and analytical techniques used for detection of polyaromatic hydrocarbons", Environ Sci Pollut Res (2017) 24, at p. 25817-25819). (Year: 2017).*

Lalaoui Noemie et al., "Wiring Laccase on Covalently Modified Graphene: Carbon Nanotube Assemblies for the Direct Bio-electrocatalytic Reduction of Oxygen", Chemistry—A European Journal, vol. 21, No. 8, Dec. 11, 2014 (Dec. 11, 2014), pp. 3198-3201, XP055819540, ISSN: 0947-6539, DOI: 10.1002/chem.201405557, Retrieived from the Internet: URL:https//onlinelibrary.wiley.com/doi/fu11-XML/10.1002/chem.201405557.

Kumar Sunil et al., "Biological and analytical techniques used for detection of polyaromatic hydrocarbons", Environmental Science and Pollution Research International, Ecomed, Landsberg, DE, vol. 24, No. 33, Oct. 14, 2017 (Oct. 14, 2017), pp. 25810-25827, XP036373232, ISSN: 0944-1344, DOI: 10.1007/S11356-017-0415-2 [retrieved on Oct. 14, 2017] "Biological methods used for the detection of PAHs".

Canas Ana I. et al., "Transformation of Polycyclic Aromatic Hydrocarbons by Laccase Is Strongly Enhanced by Phenolic Compounds Present in Soil", Environmental Science & Technology, vol. 41, No. 8, Apr. 1, 2007 (Apr. 1, 2007), pp. 2964-2971, XP055819316, US ISSN: 0013-936X, DOI: 10.1021/es062328j.

Majcherczyk Andrej et al., "Oxidation of Polycyclic Aromatic Hydrocarbons (PAH) by Laccase of Trametes Versicolor", Enzyme and Microbial Technology, Stoneham, MA, US, vol. 22, No. 5, Apr. 1, 1998 (Apr. 1, 1998), pp. 335-341, XP027537873, ISSN: 0141-0229 [retrieved on Apr. 1, 1998].

Mahmud Iqbal et al., "Electrochemical behavior of anthraquinone in aqueous solution in presence of a non-ionic surfactant", Journal of Saudi Chemical Society, Elsevier, Amsterdam, NL, vol. 15, No. 3, Aug. 31, 2010 (Aug. 31, 2010), pp. 203-208, XP028376941, ISSN: 1319-6103, DOI: 10.1016/J.JSCS.2010.08.006 [retrieved on Sep. 6, 2010].

Suma Yanasinee et al., "Enzymatic degradation of aromatic hydrocarbon intermediates using a recombinant dioxygenase immobilized onto surfactant-activated carbon nanotube", Bioresource Technology, Elsevier, Amsterdam, NL, vol. 210, Jan. 20, 2016 (Jan. 20, 2016), pp. 117-122, XP029506419, ISSN: 0960-8524, DOI: 10.1016/J.BIORTECH.2016.01.018.

Mastrangelo Giuseppe et al., "Polycyclic Aromatic Hydrocarbons and Cancer in Man", Environ Health Perspect 1996; 104:1166-70.

Goldman Radoslav et al., "Smoking Increases Carcinogenic Polycyclic Aromatic Hydrocarbons in Human Lung Tissue", Cancer Research 61, 6367-6371, Sep. 1, 2001.

Liu Kunlei et al., "Polycyclic aromatic hydrocarbon (PAH) emissions from a coal-fired pilot FBC system", Journal of Hazardous Materials B84 (2001) 175-188.

International Search Report for application No. PCT/EP2022/052472 dated Apr. 12, 2022.

* cited by examiner

METHOD FOR THE DETECTION OF POLYCYCLIC AROMATIC HYDROCARBONS

CROSS REFERENCE TO RELATED APPLICATIONS

This application is a National Stage of International Application No. PCT/EP2022/052472 having an International Filing Date of 2 Feb. 2022, which designated the United States of America, and which International Application was published under PCT Article 21(2) as WO Publication No. 2022/167479 which claims priority from and the benefit of European Patent Application No. 21305146.9, filed on 4 Feb. 2021, the disclosures of which are incorporated herein by reference in their entireties.

BACKGROUND

Field

The present disclosure concerns a method for the detection of polycyclic aromatic hydrocarbons, as well as a kit for the detection of said polycyclic aromatic hydrocarbons and a biosensor for polycyclic aromatic hydrocarbons.

Brief Description of Related Developments

Polycyclic aromatic hydrocarbons (PAHs) are among the most common organic pollutants found at contaminated industrial sites around the world. Many PAHs can have detrimental effect on the flora and fauna of affected habitats through uptake and accumulation in food chains, and in some instances, pose serious health problems and/or genetic defects in humans. PAHs, such as pyrene, benzo[a]pyrene and benz[a]anthracene have toxic, mutagenic and/or carcinogenic properties (Mastragela G, Fadda E, Marzia V. Polycyclic aromatic hydrocarbons and cancer in man. Environ Health Perspect 1996; 104:1166-70; and Goldman R, Enewold L, Pellizzari E, Beach J B, Bowman E D, Krishman S S, et al. Smoking increase carcinogenic polycyclic aromatic hydrocarbons in human lung tissue. Cancer Res 2001; 61:6367-71.).

Currently, the US. Environmental Protection Agency has classified 16 PAHs as priority pollutants whose remediation is considered indispensable for environmental clean up and human health (Liu K, Han W, Pan W P, Riley J T. Polycyclic aromatic hydrocarbon (PAH) emissions from a coal fired pilot FBC system. J Hazard Mater 2001; 84:175-88).

Current methods for PAH sensing are based on gas or liquid chromatography coupled to mass spectrometry, fluorimetry or UV-visible spectroscopy. These techniques use heavy laboratory instrumentation and/or expensive light sources.

There is thus a need for a method for PAH sensing being easy to be implemented and being also inexpensive.

DETAILED DESCRIPTION

The aim of the present disclosure is to provide a method for the detection of PAH, said method being sensitive, fast and cheap.

Another aim of the present disclosure is to provide a method for the detection of PAH, said method being easily implemented and not requiring a preliminary treatment of the sample wherein the PAH is to be detected.

Therefore, the present disclosure relates to a method for the detection of polycyclic aromatic hydrocarbons comprising:

a) a step of contacting an aqueous solution comprising at least one polycyclic aromatic hydrocarbon with a catalyst for the oxidation of polycyclic aromatic hydrocarbons and with an electrode made of a conductive porous material, and b) a step of detecting the anthraquinone that is formed during the previous step through the oxidation of the polycyclic aromatic hydrocarbons.

The method of the present disclosure thus consists in using a catalyst for the oxidation of PAH in the sample wherein the PAH is/are to be detected, said sample being in the form of an aqueous solution.

The present disclosure is based on the surprising interaction between the product obtained by the oxidation of the PAH and the conductive porous material. Indeed, it has been surprisingly observed by the inventors that the anthraquinone obtained after step a) has high adsorption properties for its interaction with the conductive porous material of the electrode.

Step a) of the method of the disclosure thus involves the use of a catalyst being able to generate quinones or semiquinones on polycyclic rings.

Said catalyst is useful for the oxidation of the PAH(s) present in the sample wherein the PAH is/are to be detected, leading then to the formation of anthraquinone, which is the product of said oxidation.

According to an aspect, the catalyst for the oxidation of polycyclic aromatic hydrocarbons is selected from the group consisting of:

- laccases and related enzymes such as copper oxidases, tyrosinases, and peroxidases);
- electrocatalysts of PAH oxidation, such as metals chosen from: Au, Pt, Ti, Ag, Pd, W, Mo, Fe, Zn, Cu or Mo and metallic alloys, metallic nanoparticles and oxides and carbon-based materials (for example charcoal, activated carbon, carbon black, carbon nanotubes and fibers, graphene);
- molecular catalysts such as iron complexes (for example porphyrins and iron chlorides), ruthenium complexes (ruthenium chloride), nickel complexes (nickel pyrazoyl), titanium complexes, vanadium complexes, or copper complexes; and
- polyoxometallates based on ruthenium, vanadium, tungsten or molybdenum.

Preferably, the catalyst for the oxidation of polycyclic aromatic hydrocarbons is a laccase.

The laccases (EC 1.10.3.2) are a family of enzymes which are found in many plants, fungi and microorganisms.

In vivo, laccases have an oxidizing activity and act as a catalyst within an enzymatic oxidation process.

The laccases which may be used in the method of the disclosure may be derived from plants, from fungi or microorganisms. The laccases stemming from fungi notably include the laccases of the *Aspergillus, Neurospora* (for example *Crassa Neurospora*), *Podospora, Botrytis, Collybia, Fomes, Lentinus, Pleurotus, Trametes* (for example *Trametes villosa* and *Trametes versicolor*), *Rhizoctonia* (for example *Rhizoctonia solani*), *Coprinus* (for example *Coprinus cinereus, Coprinus comatus, Coprinus friesii* and *Coprinus plicatilis*), *Psathyrella* (for example *Psathyrella condelleana*), *Panaeolus* (for example *Panaeolus papilionaceus*), *Myceliophthora* (for example *Myceliophthora thermophila*), *Scytalidium* (for example *Scytalidium thermophilum*), *Polyporus* (for example *Polyporus pinsitus*), *Phlebia* (for example *Radiata phlebia*), *Pycnoporus* (for example *Pycnoporus cinnabarinus*) or *Coriolus* (for example *Coriolus hirsutus*) genera. The laccases stemming from bacteria stem for example from *Bacillus*.

Preferably, a laccase stemming from *Trametes versicolor*, marketed by Sigma Aldrich is used.

Concentrations of catalyst used within the disclosure modify the conversion rate of the PAH into a redox-active detectable compound. Preferably, the catalyst concentrations, in particular the laccase concentrations, when used in solution, range between 1 and 1000 U $mL^{-1}$.

As mentioned above, the method of the present disclosure also involves the use of an electrode made of a conductive porous material.

According to the disclosure, the term "conductive material" refers to a material which allows the flow of electrons in one or more directions across its structure. Conductivity of these materials is given by its electrical conductivity in Siemens and its electrical resistivity in ohm·meter According to the disclosure, the term "porous material" refers to a material comprising at least one pore, preferably several pores, said pore(s) having a size comprised from 1 nm to 1 mm. Porosity can be given by measuring the specific surface area of the material by gas physical adsorption giving access to the BET surface which can be typically comprised between 1 and 5000 $m^2$ $g^{-1}$.

According to an aspect, the conductive porous material is selected from the group consisting of: carbon-based conductive material, conductive polymers and metals and corresponding metal oxides.

As carbon-based conductive material, the followings may be mentioned: carbon nanotubes, graphene, activated charcoal, carbon black, carbon pastes, and graphite.

As conductive polymers, the followings may be mentioned: polypyrroles, polythiophene, polyvinyl, polyacetylenes, polyindoles, polyanilines, polyphenylenes, and polypyrenes.

As metals, the followings may be mentioned: Au, Pt, Ti, Ag, Pd, W, Mo, Fe, Zn, Cu and Mo.

Preferably, the electrode made of a conductive porous material for step a) is an electrode made of carbon nanotubes. The electrode can be hard disks of 1 μm to 1 cm, screen-printed electrodes, flexible paper or bucky-paper electrodes, microelectrodes, microelectrode arrays, microneedles, nanoneedles, or Field-Effect-Transistor electrodes.

Step a) as defined above is then followed by a detection step, consisting in the detection of the anthraquinone that is formed during the previous step through the oxidation of the polycyclic aromatic hydrocarbons.

According to an aspect, said catalyst is put in the presence of the solution to be analyzed which contains the targeted PAH (in particular anthracene). The catalyst triggers the oxidation of the PAH (anthracene) into a quinoid product which is redox-active (in particular anthraquinone). Said conductive material is put in the presence of the solution containing the oxidized product. The conductive material affords the adsorption of the product and its detection by electrochemistry.

As PAH able to be detected according to the present method, the following compounds may be mentioned: Naphtalene, Benzo(k)fluoranthene, Acenaphtene, Benzo(a) pyrene, Acenaphtylene, Dibenz(a,h)anthracene, Fluorene, Benzo(ghi)perylene, Phenanthrene, Indeno(1,2,3-cd)pyrene, anthracene, Fluoranthene, Pyrene, Benz(a)anthracene, Chrysene, Benzo(k)fluoranthene, perylene, and coronene.

According to a particular aspect, step a) of the method according to the present disclosure further comprises the addition of a redox compound.

Preferably, the redox compound is selected from the group consisting of: 2,2'-azino-bis(3-ethylbenzothiazoline-6-sulfonic acid)(ABTS), (2,2,6,6-tetramethyl-piperidin-1-yl)oxy (TEMPO), osmium complexes, quinones, metallocenes such as ferrocenes, and mixtures thereof.

The use of such redox compound is advantageous in that it facilitates the oxidation reaction and also in that the method of the disclosure is more sensitive.

Preferably, the concentration of the redox compound is between 1 nM and 500 mM.

According to an aspect, the catalyst for the oxidation of polycyclic aromatic hydrocarbons as defined above is immobilized on the electrode.

In such aspect, step a) thus consists in contacting the aqueous solution (or sample) comprising at least one polycyclic aromatic hydrocarbon with the electrode (on which is immobilized the catalyst as defined above).

This specific aspect has the advantage to be even more simple by combining both the catalyst and the electrode material in the same surface for a rapid detection method.

The present disclosure also relates to a kit for the detection of polycyclic aromatic hydrocarbons comprising:

- an electrode made of a conductive porous material as defined above, and
- a catalyst for the oxidation of polycyclic aromatic hydrocarbons as defined above.

Preferably, the kit according to the disclosure comprises an electrode made of carbon nanotubes and a laccase.

The present disclosure also relates to a biosensor for polycyclic aromatic hydrocarbons, said biosensor comprising an electrode made of a conductive porous material as defined above, on which a catalyst for the oxidation of polycyclic aromatic hydrocarbons as defined above is immobilized.

A preferred biosensor according to the present disclosure comprises an electrode made of carbon nanotubes, on which a laccase is immobilized.

EXAMPLES

Materials and Methods

Reagents

All reagents were purchased from Sigma-Aldrich (Saint Louis, Missouri, USA) and were used without further purification. All chemicals employed were of analytical grade. Distilled water was passed through a Milli-Q water purification system to obtain 18.2 MΩ $cm^{-1}$ ultrapure water. Phosphate/citrate (Mcilvaine) and Tris-HCl buffer solutions ware prepared from Milli-Q water.

Electrochemical Measurements

The electrochemical experiments were carried out in a three-electrode electrochemical cell using a Biologic VMP3 Multi Potentiostat. The saturated calomel electrode (SCE) served as the reference electrode, a Pt wire was used as the counter electrode and MWCNT bioelectrodes were used as working electrodes. All experiments were conducted at room temperature. All simulated curves were obtained via Origin Pro 9.0. Error bars were estimated from three measurements recorded per sample.

Preparation of the Glassy Carbon-Modified MWCNT Electrode

The working electrodes were glassy carbon electrodes (3 mm diameter). 5 mg/mL NMP dispersions of MWCNTs (Multi-Walled Carbon Nanotube, purity >99% Sigma-Aldrich) were prepared by 30 min in ultrasonic bath (Fisher scientific FB 15050) until homogeneous black suspension was obtained. Then 20 μL of the MWCNTs solution were drop-casted on a GCE and NMP was removed under vacuum obtaining a 5-μm-thick film.

Laccase Enzymes

The laccase activity was assayed at room temperature, monitoring the oxidation of ABTS (2,2'-azino-bis(3-ethylbenzothiazoline-6-sulphonic acid)) at 420 nm (ε420 nm=$3.6\times10^4$ $M^{-1}$ $cm^{-1}$)—the assay mixture contained 2 mM ABTS and 50 mM phosphate/citrate buffer, pH 3.0.

PAH Biosensing

Figure 1:
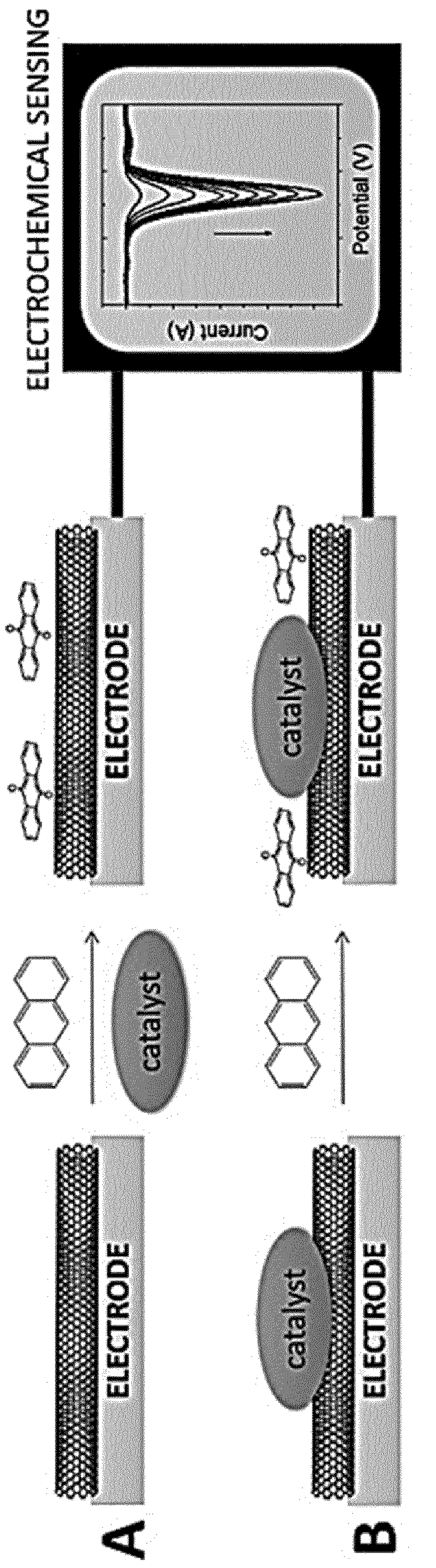
FIG. 1. Principle of the PAH sensor according to the disclosure based on (A) catalyst (such as laccase) in solution and (B) immobilized on the electrode (such as an electrode made of carbon nanotubes).
Figure 2:
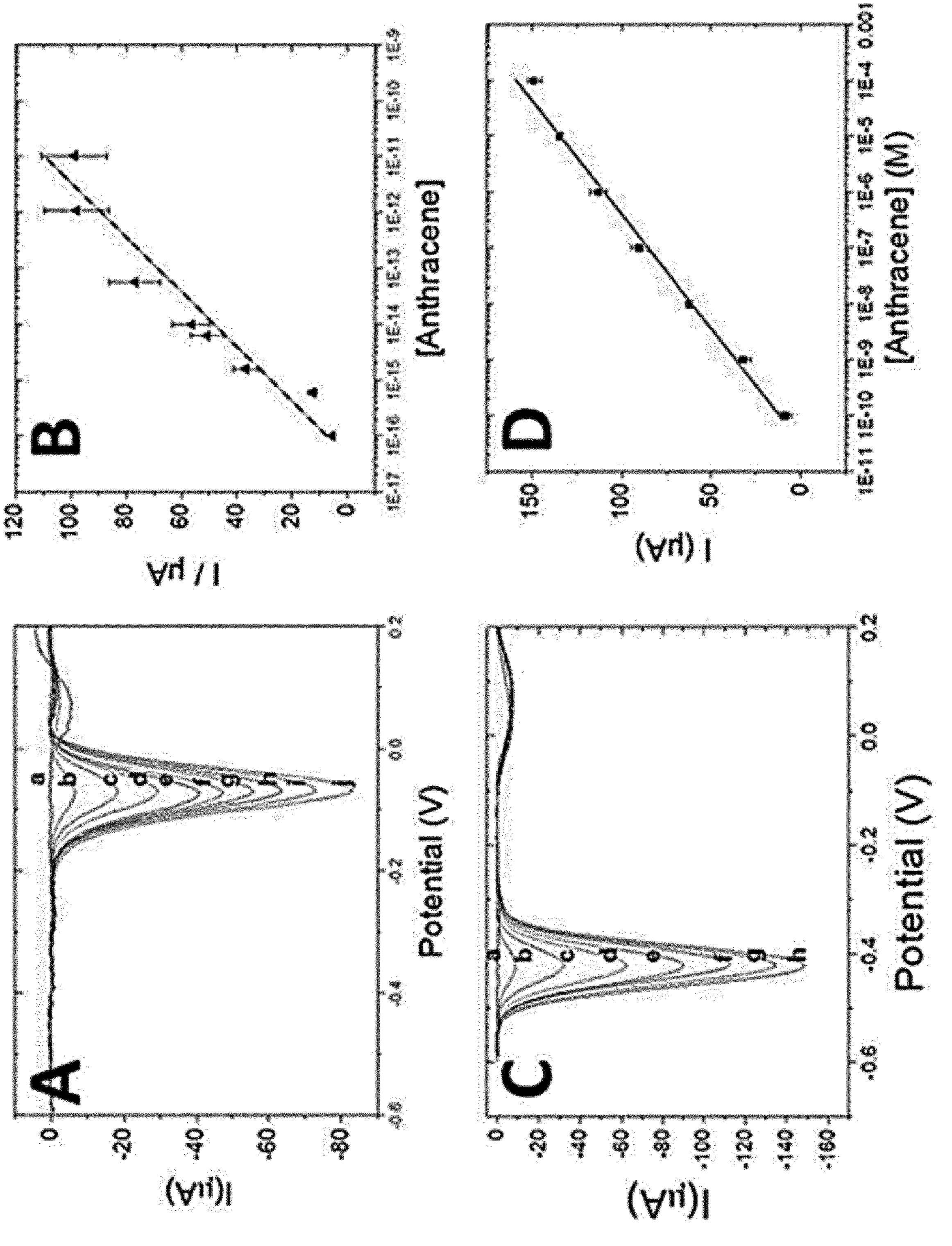
FIG. 2. (A) Electrochemical detection of different concentrations of anthracene solutions (a: 0, b: 0.1 fM, c: 0.5 fM, d: 1 fM, e: 10 fM, f: 50 fM, g: 0.1 pM, h: 1 pM, i: 10 pM, and j: 50 pM) obtained with laccase in solution by SWV (0.1 M McIlvaine buffer pH 5, 25° C., ref Ag/AgCl, pulse height=25 mV, pulse width=0.5 s, step height=−5 mV); (B) corresponding linear logarithmic scale between 0.1 fM and 50 pM; (C) Electrochemical detection of different concentrations of anthracene solutions (a: 0, b: 0.1 nM, c: 1 nM, d: 10 nM, e: 0.1 μM, f: 1 μM, g: 10 μM and h: 100 μM) obtained with immobilized laccase by SWV (0.1 M McIlvaine buffer pH 5, 25° C., ref Ag/AgCl, pulse height=25 mV, pulse width=0.5 s, step height=−5 mV); and (D) corresponding linear logarithmic scale between 0.1 nM and 0.1 μM.
Figure 3:
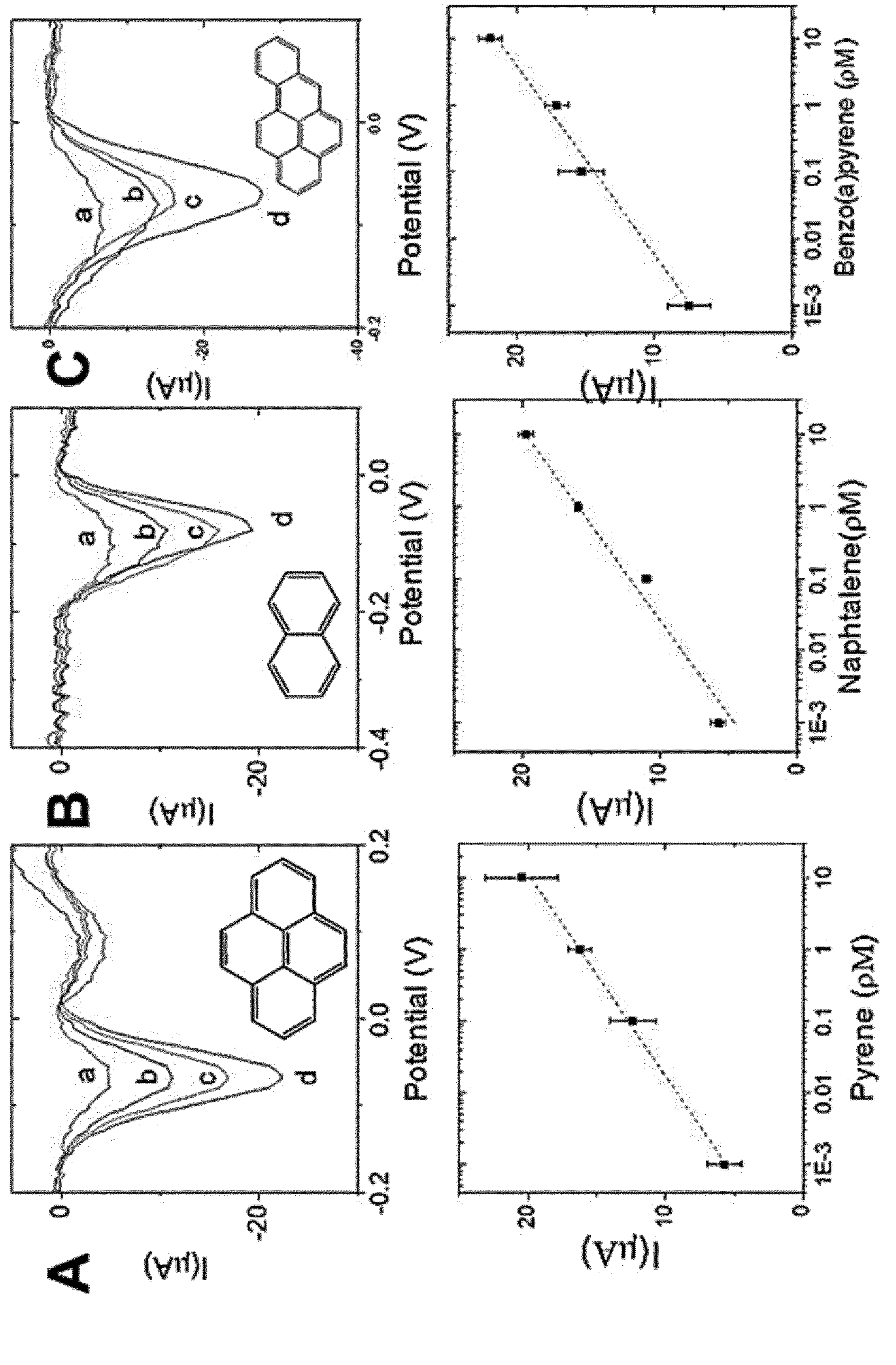
FIG. 3. (A) Electrochemical detection of different concentrations of pyrene, naphthalene and benzo(a)pyrene solutions (a: 0.001, b: 0.1 c: 1, and d: 10 pM) obtained with laccase in solution by SWV (0.1 M McIlvaine buffer pH 5, 25° C., ref Ag/AgCl, pulse height=25 mV, pulse width=0.5 s, step height=−5 mV) and (B) corresponding linear logarithmic scale between 1 fM et 10 pM.

Two different strategies have been set up:

Laccase in Solution (FIGS. 2A and B, FIG. 3)

A reaction solution was prepared with 2 U of laccase, 0.01 mM ABTS as a redox mediator in phosphate/citrate (2 mL at pH=5) at increasing PAH concentrations (from 0 to 1 mM) and incubated at room temperature for 1 hour. MWCNT electrodes were immersed in the reaction solution for 10 minutes, and the detection of as-produced and adsorbed oxidized products were measured by SWV in a phosphate/citrate buffer solution pH 5.

40° C./No ABTS, Immobilized Enzyme (FIGS. 2C and 2D)

In the second developed assay to detect PAHs, the modified MWCNT electrodes were incubated in 20 μL of laccase (100 U/mL) for 2 h at room temperature. Electrodes were then rinsed with 50 mM Tris-HCl buffer solution at pH=8 and stored at 4° C. The modified bioelectrodes were immersed in a phosphate/citrate buffer solution (2 mL at pH=5) at increasing concentrations of Anthracene (from 0 to 1 mM) and incubated at 40° C. for 2 h. Then, the detection of as-produced and adsorbed oxidized products were measured by SWV in a phosphate/citrate buffer solution pH 5.

What is claimed is:

1. A method for the detection of polycyclic aromatic hydrocarbons comprising:

a) a step of contacting an aqueous solution comprising at least one polycyclic aromatic hydrocarbon with a catalyst for the oxidation of polycyclic aromatic hydrocarbons and with an electrode made of a conductive porous material, and b) a step of detecting the anthraquinone that is formed during the previous step through the oxidation of the polycyclic aromatic hydrocarbons.

2. The method of claim 1, wherein the catalyst for the oxidation of polycyclic aromatic hydrocarbons is selected from the group consisting of: laccases and related enzymes, electrocatalysts of PAH oxidation, molecular catalysts, polyoxometallates based on ruthenium, vanadium, tungsten or molybdenum, and mixtures thereof.

3. The method of claim 1, wherein the catalyst for the oxidation of polycyclic aromatic hydrocarbons is a laccase.

4. The method of claim 1, wherein the conductive porous material is selected from the group consisting of: carbon-based conductive materials, conductive polymers, and metals and corresponding metal oxides.

5. The method of claim 1, wherein the electrode made of a conductive porous material is an electrode made of carbon nanotubes.

6. The method of claim 1, wherein step a) further comprises the addition of a redox compound.

7. The method of claim 6, wherein the redox compound is selected from the group consisting of: 2,2'-azino-bis(3-ethylbenzothiazoline-6-sulfonic acid)(ABTS), (2,2,6,6-tetramethylpiperidin-1-yl)oxy (TEMPO), osmium complexes, quinones and metallocenes.

8. The method of claim 1, wherein the catalyst for the oxidation of polycyclic aromatic hydrocarbons is immobilized on the electrode.

9. A kit for the detection of polycyclic aromatic hydrocarbons comprising:

an electrode made of the conductive porous material, and the catalyst for the oxidation of polycyclic aromatic hydrocarbons wherein the kit is configured to implement the method of claim 1.

10. A biosensor for polycyclic aromatic hydrocarbons comprising an electrode made of the conductive porous material, on which the catalyst for the oxidation of polycyclic aromatic hydrocarbons is immobilized wherein the biosensor is configured to implement the method of claim 1.

* * * * *